United States Patent
Rapetti Mogol et al.

(10) Patent No.: US 10,024,699 B2
(45) Date of Patent: Jul. 17, 2018

(54) DEVICE AND METHOD FOR DYNAMICALLY MEASURING AN ENVIROMENTAL QUALITY FACTOR

(71) Applicant: CASALIFE S.R.L., Milan (IT)

(72) Inventors: Francesco Rapetti Mogol, Oristano (IT); Marco Magnarosa, Pisa (IT); Alessandro Mandelli, Segrate (IT)

(73) Assignee: NUVAP S.R.L., Cascina (Pisa) (IT)

( * ) Notice: Subject to any disclaimer, the term of this patent is extended or adjusted under 35 U.S.C. 154(b) by 892 days.

(21) Appl. No.: 14/400,882

(22) PCT Filed: Mar. 5, 2013

(86) PCT No.: PCT/IT2013/000068
§ 371 (c)(1),
(2) Date: Nov. 13, 2014

(87) PCT Pub. No.: WO2014/073010
PCT Pub. Date: May 15, 2014

(65) Prior Publication Data
US 2015/0127292 A1    May 7, 2015

(30) Foreign Application Priority Data
Nov. 6, 2012 (IT) ................. FI2012A0238

(51) Int. Cl.
*G01D 21/02* (2006.01)
*G01N 33/00* (2006.01)
(Continued)

(52) U.S. Cl.
CPC ............. *G01D 21/02* (2013.01); *F24F 11/30* (2018.01); *G01N 33/0004* (2013.01);
(Continued)

(58) Field of Classification Search
CPC .................. G01D 21/02; G01R 29/08
See application file for complete search history.

(56) References Cited

U.S. PATENT DOCUMENTS 9,154,559 B1 * 10/2015 Bovee .............. H04L 67/16
2006/0071773 A1 * 4/2006 Ahmed ............. A01K 1/031
340/521
(Continued)

FOREIGN PATENT DOCUMENTS

| EP | 1 275 908 A1 | 1/2003 |
|---|---|---|
| WO | 94/14014 A1 | 6/1994 |
| WO | 2007/027631 A1 | 3/2007 |

OTHER PUBLICATIONS

International Search Report, dated Jul. 25, 2013, from corresponding PCT application.

*Primary Examiner* — Michael Dalbo
(74) *Attorney, Agent, or Firm* — Young & Thompson

(57) ABSTRACT

A device and apparatus for measuring and monitoring a domestic environment, include a plurality of sensors (SD11-Snm) for measuring local environmental parameters, a remote source (INFO) of data that can be associated to the environmental quality factor, control elements (CX) for controlling the current conditions of the domestic environment being monitored, further including a programmable electronic processing unit for processing dynamically, via an adaptive algorithm, a current value of the quality factor on the basis of the local-measurement data, of the remote data associated to the quality parameter, and of the local environmental conditions.

12 Claims, 2 Drawing Sheets

(51) Int. Cl.
*G01N 33/18* (2006.01)
*G01R 29/08* (2006.01)
*F24F 11/30* (2018.01)
*F24F 11/52* (2018.01)
*F24F 110/50* (2018.01)
*F24F 110/68* (2018.01)

(52) U.S. Cl.
CPC ............ *G01N 33/18* (2013.01); *G01R 29/08* (2013.01); *F24F 11/52* (2018.01); *F24F 2110/50* (2018.01); *F24F 2110/68* (2018.01); *Y02B 30/78* (2013.01)

(56) References Cited

U.S. PATENT DOCUMENTS

| | | | | |
|---|---|---|---|---|
| 2006/0242679 | A1* | 10/2006 | Hutchison, III | H04N 7/17318 725/105 |
| 2007/0100479 | A1* | 5/2007 | Ahmed | G05B 15/02 700/47 |
| 2009/0055120 | A1* | 2/2009 | Vickery | G01D 3/022 702/104 |
| 2010/0158903 | A1* | 6/2010 | Smith | A61K 39/00 424/133.1 |

* cited by examiner

DEVICE AND METHOD FOR DYNAMICALLY MEASURING AN ENVIROMENTAL QUALITY FACTOR

TECHNICAL SECTOR

The present invention relates to a system for domestic monitoring of environmental quality through joint detection of various environmental parameters such as, by way of example, 100-kHz to 3-GHz electromagnetic fields, low-frequency electromagnetic fields, radon, water composition, fine dust, $CO_2$, noise.

In particular, the invention relates to a monitoring system that dynamically integrates local environmental measurements and information that can be obtained remotely, relevant for quantification of a domestic environmental quality factor, understood as value that determines the overall quality of the domestic environment being monitored.

PRIOR ART

In the current state of the art, monitoring systems are known for environmental detection and for measurement of surrounding environmental parameters, as well as techniques and sensors that are already available on the market.

Said systems, however, are not suited to a domestic environment. Typically, in fact, they detect data out of doors or in specific conditions, and moreover are used individually for detecting a single environmental parameter.

Finally, processing of the data is not performed dynamically and does not take into account either new general information that determines new assessments of the results obtained or the historic memory of this information, or again information present in field at that given moment.

Basically, known systems are based upon devices that are off-line with respect to the relevant information available on the web, or that in any case do not draw information from other on-line databases of sensors and devices or from the web and from social networks.

Moreover, for the sensor networks present on the market it is very difficult to have a specific mode of reliable detection of data in so far as it is not possible to determine with certainty that the detection is made in valid and repeatable measuring conditions unless a specialized operator is present.

PURPOSE OF THE INVENTION

With the present invention, the aim is to overcome the drawbacks of already known solutions and to propose a domestic environmental monitoring apparatus that will be reliable and able to improve over time thanks to dynamic detection and interpretation of significant data.

SUMMARY OF THE INVENTION

The above purposes have been achieved by providing a device and an apparatus according to at least one of the annexed claims.

The device and the apparatus of the invention envisage, in particular, integrated processing of local-measurement data and data external to the environment monitored, via an adaptive/genetic algorithm, which, detecting the data in a reliable way, processes them according to the historic memory, to the specific data available in real time, such as for example medical and environmental research that will determine risk factors, social-advertising data available on the web, for example regarding the "social reputation" on the Internet on issues relevant to environmental monitoring.

A first advantage lies in the fact that the invention envisages a functional architecture and a corresponding algorithm of analysis of the data that guarantee in an overt way the best possible quality of the information for the user and on-line updating of the system, it being possible to intervene with functional modifications on the basis of information present on the web (medical and environmental data, data from other sensor networks, data from the web and from social networks, etc.). The invention consequently integrates different sensors in a single measuring system and determines a measuring method specialized for the individual domestic environment that is based on the data received from the different sensors.

A second advantage lies in the fact that the device of the invention can be set for unifying the different types of sensors, which may already be present on the market, but aggregating them together via a central system capable of detecting all the data and gathering them in an integrated way.

A third advantage lies in providing a system for controlling local-measurement data that guarantees the effective validity and repeatability thereof, without the presence in situ of a specialized technician, but through an automated detection of situations of unsatisfactory measurement.

LIST OF THE DRAWINGS

The above and further advantages will be better understood by any person skilled in the branch from the ensuing description and from the annexed drawings, which are provided by way of non-limiting example and in which.

DETAILED DESCRIPTION

Figure 2:
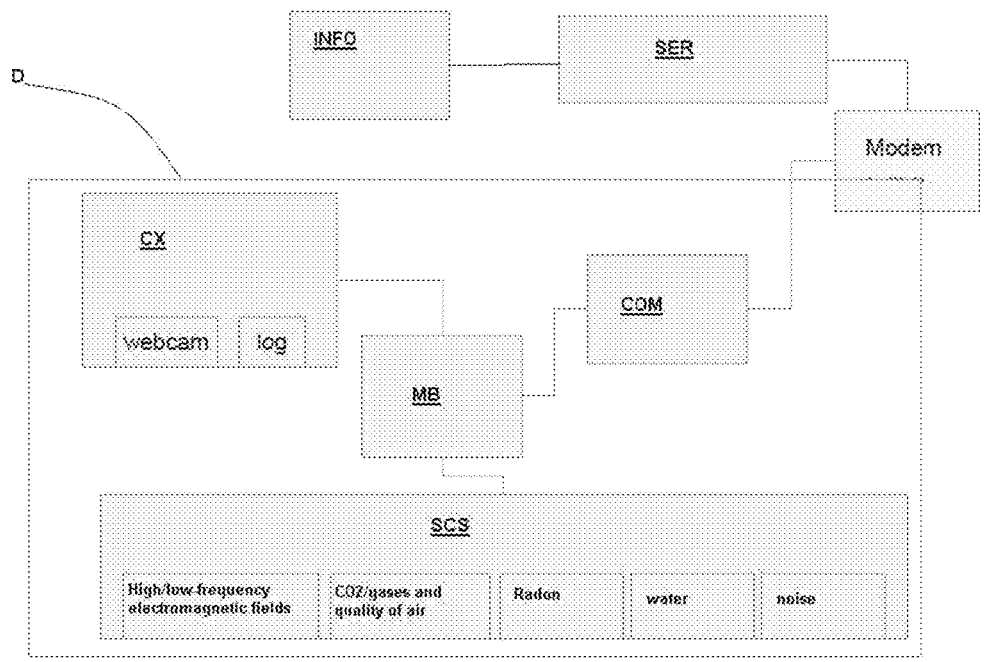
FIG. 2 is a schematic illustration of a local device according to the invention.

With reference to the attached drawings, and in particular to FIG. 2, an electronic device D for measuring and monitoring a domestic environment is described.

The device D comprises a plurality of sensors S1-Sm for measuring local environmental parameters FQP1-FQPm that can be associated to a local environmental quality factor FQ, understood as the time-variable value that determines the current overall quality of the domestic environment or dwelling being measured by the device D1-Dn present in said domestic environment being monitored.

Preferably, the sensors S1-Sm are sensors for measuring 100-kHz to 3-GHz electromagnetic fields;

low-frequency electromagnetic fields;

radon;

the composition of water;

fine dust;

$CO_2$;

noise and in general each parameter that is significant for the quality of the domestic environment.

Preferably, the device is provided with an electronic card SCS that is able to interface sensors S1-Sm that use even non-uniform measuring methods and to process the measurement data in an integrated way through a single integration software and a single hardware through different standard connections (electronic connectors, serial connectors, USBs).

The sensors S1-Sm are connected to a programmable electronic processing unit MB, which is in turn connected to a data-exchange interface MODEM, preferably via a secure communication module COM.

The unit MB is moreover connected to a remote-data source INFO containing data that can be associated to a local environmental quality factor FQP regarding the environment being monitored and to a control system CX capable of monitoring the current local environmental conditions that interfere with the local environmental parameters measured.

According to the invention, the programmable unit MB is programmed for receiving repeatedly in time measurement data of the local parameters measured by the sensors S1-Sm, remote data associated to the factor FQP received from the data source INFO, and data regarding the current local environmental conditions received by the control system CX, and for processing dynamically said data by means of an adaptive algorithm and for calculating a value of the factor FQP.

Advantageously, the adaptive algorithm provides the user with the highest quality possible of the information and a continuous updating of the devices with the corresponding appropriate functional modifications (for example, variations in the importance of a certain parameter or of an environmental condition) that can be derived from the accessible information.

Preferably, the data source INFO is constituted by contents present on the Internet (for example, medical and environmental data, data from other sensor networks, data from the web and from social networks, etc.), but may comprise data present or not in various private databases.

The control means CX may comprise a rotary webcam (WEBCAM) and means for collecting historic data (LOG) in order to determine the effective validity and repeatability of the measurements made. In particular, the webcam is set for analysing the local environmental images and detecting the effective reliability of the measuring methods in a point-by-point way at least during the measurement steps, recognizing any possible malfunctioning and errors, processing the data locally, and sending the information, preferably on an independent data-exchange channel, to a remote central control unit SER. The central control unit can thus analyse the data received, detecting any possible measurement anomalies.

In greater detail, during the measuring steps the rotary webcam carries out collection of the images through 360° and processing thereof through motion-detection techniques that determine endogenous and exogenous phenomena that prevent proper detection of the measurement parameters by the sensor card SCS and the sensors themselves. Said phenomena will be detected in situ through processing of the data by the processing units MB of the devices and will be notified and processed also by the central control unit SER in order to collect all the information on specific conditions of malfunctioning. Locally, the device will have available all the information of events that vitiate the measurements present in the central database and hence will be able to process directly the information locally.

Periodically (at each updating) the central system SER will be able to upgrade the information on the device.

Figure 1:
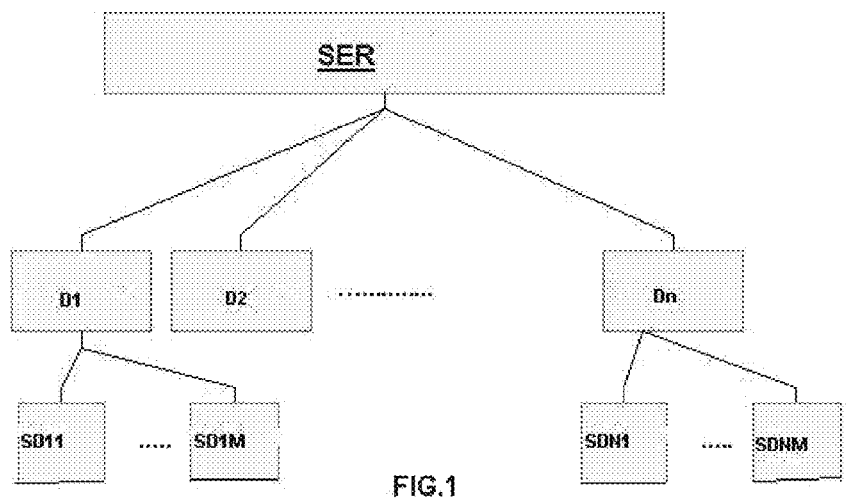
FIG. 1 is a schematic illustration of an apparatus according to the invention.

With reference to FIG. 1, illustrated schematically is an apparatus according to the invention comprising local devices D1-Dn of the type described above connected via the interface MODEM to a remote central control unit SER, which in turn communicates with a remote source INFO containing measurement data of local environmental parameters.

Appearing hereinafter is an example of calculation of the quality factor FQP regarding the example illustrated, i.e., for an apparatus provided with devices D1-Dn equipped with sensors SD11-SDnm.

Example of Calculation of FQP

The quality factor ($FQP_k((t))$) of the k-th device (at the time of measurement t=T) is the sum of the quality factors of each individual sensor of the device ($FQP_{kx}(t)$) weighted by means of coefficients ($\alpha_x(t)$), the value of which, determines the relative higher or lower relevance in the final result $$FQP_k = \sum_{x=1}^{N} a_x(t) FQP_{kx}(t)$$

$$FQP_k(T) = \sum_{x=1}^{N} a_x(T) FQP_{kx}(T)$$

where:
N is the number of sensors for each individual device;
M is the number of devices used;
N=M;
t is the time as discrete variable;
T is the time of the last measurement made;
$FQP_k$ is the quality factor for the k-th device;
$FQP_{kx}$ is the quality factor for the x-th sensor of the k-th device.

The quality factor of the k-th device is hence a value that ranges from 0 to N, where 0 is a low level of environmental quality and N a high level of environmental quality, given by the sum of the quality factors of the individual sensors x for each device. Said factors are given by the ratio between the value of the parameter of the sensor ($Vsd_{kx}(t)$) and the maximum value of said parameter over all the sensors present.

$$0 \le FQP_{kx}(t) \le 1 \quad FQP_{kx}(t) = \frac{Vsd_{kx}(t)}{\max_{k(1,M)} Vsd_x}$$

where
$Vsd_{kx}(t)$ is the value of the parameter (sensor) x of the k-th device at time t;

$$\max_{k(1,N)} Vsd_x$$

is the maximum value of the parameter (sensor) x, which is a constant obtained from calibration calculations of the specific sensor $$\sum_{x=0}^{N} a_x(t) = N$$

$a_x(t)$ is the quality coefficient of sensor x with respect to other N−1 active sensors on a k-th device at time T $0 \leq a_x(t) \leq N$ The quality coefficient is hence a value that conditions also the other values for the k-th device. In fact, the sum of all the coefficients of a k-th device is always equal to N.

$a_x(T) = a_x(T-1) + \Delta_x(T)$ $\Delta_x(T) = f_x(a_x(T), a_x(T-1),$ Number of measurements made (T,T−1), Number of relevant medical reviews validated (T,T−1),
Number of reviews on search engines (T,T−1),
Medical data (T), Environmental data (T), geographical position)

$$\sum_{x=0}^{N} \Delta_{Kx}(t) = 0$$

$$\Delta_{kx}(t) \leq \Delta_{KMAX}(t)$$

$\Delta_{Kx}(t)$ is the Darwin variation factor of the K-th device $\Delta_{MAX}(t) = f(\text{medical data, environmental data, geographical position } t, t-1)$ is the maximum value of variation Darwin delta ($\Delta_x(T)$) is a corrective factor of the quality coefficient that modifies said factor as a function of a set of parameters and through the application of an adaptive algorithm $f_x$. Said algorithm determines the prevalence of the dominant values from among those obtained at times T and T−1 and as a function of specific variables and of constant values given by the system.

The maximum value with which the quality coefficients may vary ($\Delta_{MAX}(t)$) is variable as a function of the information deriving from the risks and hazards of a given parameter in a given geographical area.

An example of adaptive algorithm that may be applied to the system of the invention is the following adaptive function $$\Delta_{Kx}(t) = f(t)$$

$$= \left( \frac{\sum_{y=1}^{N} \frac{\beta_{Ky}(t) Pr_{Kxy}(t)}{|Pr_{Kxy}Tot(t)|}}{\text{average}\left|\sum_{y=1}^{N} \frac{\beta_{Ky}(t) Pr_{xy}(t)}{|Pr_{xy}Tot(t)|}\right|} \right) \cdot \Delta_{MAX}(t)$$

where:

$Pr_{Kxy}(t)$ is the parameter y of the sensor x of the k-th device;

$Pr_{xy}Tot(t)$ is the sum of the value $Pr_{xy}$ of all the sensors:

$$Pr_{xy}Tot(t) = \sum_{x=1}^{N} Pr_{xy}(t);$$

$\beta_{Ky}(t)$ is the coefficient of adaptation for the individual parameter of the k-th sensor. For example, the parameters may be:

$Pr_{Kx1}(T)$, which is the number of measurements made at times T and T−1;

$Pr_{Kx2}(T)$, which is the number of sensors functioning at times T and T−1;

$Pr_{Kx3}(T)$, which is the number of reviews on keywords at times T and T−1;

$Pr_{Kx4}(T)$, which is the number of user reviews on specialized websites at times T and T−1;

$Pr_{Kx5}(T)$, which are the medical and environmental data at times T and T−1;

$Pr_{Kx6}(T)$, which are the data of individual sensors of each device from time 0 to time T.

The above parameters will in any case continuously evolve and be modified in relation to the different applications of the invention.

It is understood that the type of the adaptive algorithm may be in any case varied as a function of the evolution of the applications and of the population of the sensors. In one embodiment of the invention the adaptive algorithm is also based upon the "social" data coming from the web such as, for example, the number of reviews on a given subject, for given keywords, or else an element of assessment of the quality of the measurement.

The apparatus described is suited to applications of different types.

The typical use of the system is that of a distributed network of sensors and measurements that gathers data from the individual sensors present in different positions over the territory to characterize better the information supplied by the local sensor. In this sense, it is possible to distinguish two types of typical application:

device for point measurement in the case where measurements are made in different discrete times;
device for distributed measurement in the case where the measurements are made continuously.

In the former case, the measurements may be made in a point-by-point way in different places, and the data obtained may be processed remotely by the unit SER and made available to the individual devices D for improvement of the adaptive algorithm used in the subsequent measurements.

In the latter case, the measurements are made continuously and at the same time on all the sensors of the apparatus, and hence the data are used all together for improving the adaptive algorithm used in the subsequent measurements.

The algorithm may moreover be improved on the basis of information received from a sensors network with both types of application.

Moreover, the two types of applications require the use of different types of sensors for detecting one and the same parameter.

In the former case, if the measurement is a point measurement, i.e., made just once in a given point, the type of sensor used must be a high-quality sensor so as to have a valid detection and not falsify the entire data population.

In the latter case, instead, seeing that the measurements are made continuously in a given place, it is possible to use lower-quality sensors in so far as the historic datum of the space being measured is available.

Advantageously, to one and the same system there may hence be applied sensors of higher or lower quality, i.e., ones that determine a better or worse quality of point measurement because the adaptive algorithm will know this aspect and will weigh the level of precision of the measurement in the scale of importance given to the measurement within the adaptive algorithm.

The dynamic calculation made with the algorithm may moreover comprise the calculation of data deriving from the historic memory of previous measurements coming from sensors that are already installed.

Via the time-adaptive algorithm it will be moreover possible to modify also the methodologies of measurement and the corresponding sensors, or add new ones. The datum processed will in any case be the sum of different parameters and adapted as a function also of the number of measurements made and of the quality of the sensor.

Example 1: Device for Point Measurement

This is a testing device for specialized operators.

Via this system, an operator prepares a measurement set-up, positions the sensors within a dwelling according to the specifications envisaged by the measuring procedure, and starts the measurement itself. At this moment, the measurement and control system is activated. If the data detected are congruous, they are sent on the web, analysed, and processed by the central system. A certificate of analysis and environmental quality is then issued by the central system, which is possibly sent to the end user.

With this system services of home screening may be provided, which are carried out by specialized operators using the device that implements the invention.

Example 2: Device for Distributed Measurement

This is a device to be located in the dwelling for round-the-clock environmental control of polluting agents.

The above device may also be integrated during building or restructuring of the house, and through a display of the data or through the domotic system provided it will be possible to display the point-measurement data.

The device detects the point data through the measurement sensors, checks that the measurements have been made correctly, and processes the data in situ to ensure a level of quality for the environment in which it is located. Next, through connection via the Internet, it sends the data on the web and receives from the central system a feedback on the level of overall quality. Said information is then made available to the end users according to the various modalities (SMS, web, display, etc.)

Figure 3:
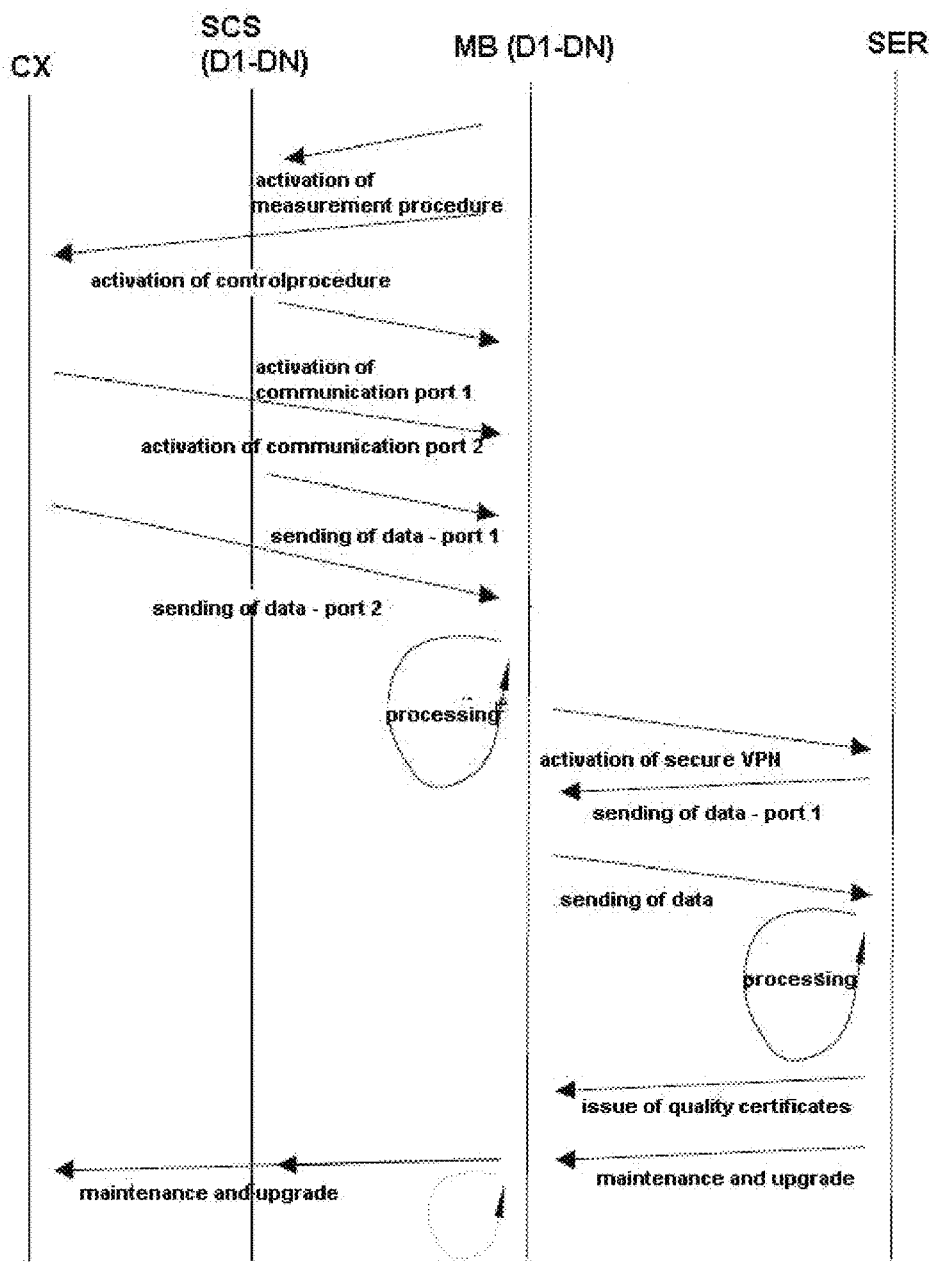
FIG. 3 shows a schematic diagram of operation and data exchange between the components of the apparatus of FIG. 1.

FIG. 3 represents schematically operation of the apparatus and data exchange between the devices and the central control unit.

Preferably, the information exchanged will have to be processed locally by the units MB of the devices and sent back to the central control unit SER via an ADSL/WiFi/3G/4G Internet connection in a secure form, for example a secure encoding mode based upon standard security algorithms and transmission modes of a VPN (Virtual Private Network) type. In a preferred example of embodiment, there will be two VPNs, which are distinct according to whether the data are data that regard the measurements made by the sensors SD or data transmitted by the control system CX, regarding control operations.

The various devices of the system communicate with one another according to the operating scheme described in FIG. 3.

In particular, periodically activated by the motherboard MB of the device in relation to the timing of the measurement, the sensors SD and the control system Cx are activated for detecting the measurement data and the data regarding proper configuration of the measuring environment itself. These data are sent to the motherboard MB through different communication ports and processed by the motherboard in situ. Said processing is expedient to prevent problems of connection to the central system SER from vitiating at least a first local evaluation of the data and likewise to prevent problems of privacy on the control data, which are not sent back onto the web in the case where they are not required by the user of the service. The data are sent to the central system SER in a secure way, where they are processed and definitively filed in the system database. Periodically, on the basis of the data received, the central system SER may send data for activation of procedures of calibration, maintenance, and upgrading of the system.

The present invention has been described according to preferred embodiments, but equivalent variants may be devised, without thereby departing from the sphere of protection granted.

The invention claimed is:

1. A device (D1-Dn) for measuring and monitoring a domestic environment, comprising:
   a plurality of sensors (SD11-Snm) for measuring local environmental parameters relevant for the value of an environmental quality factor (FQP1-FQPn) of the domestic environment being monitored;
   receiving means for receiving from a remote source (INFO) data that can be associated to the local environmental quality factor (FQP1-FQPn);
   control means (CX) for controlling the current conditions of the domestic environment monitored that interfere with the local environmental parameters measured; and
   a first programmable electronic processing unit (MB), operatively connected to said sensors (SD11-SDnm), to said receiving means and to said control means (CX) for receiving repeatedly in time measurement data of the local parameters, remote data associated to the factor (FQP1-FQPn), data regarding the current local environmental conditions, the unit (MB) being moreover programmed for processing dynamically, by means of an adaptive algorithm, a current value of the factor (FQP1-FQPn) on the basis of the local-measurement data, of remote data associated to the parameter, and of the current local environmental conditions;
   wherein said sensors (SD11-SDnm) are integrated in a single electronic card (SCS) operatively connected to said processing unit, and comprise sensors for detecting electromagnetic fields of from 100 kHz to 3 GHz, low-frequency electromagnetic fields, radon, water composition, fine dust, $CO_2$, and noise.

2. The device according to claim 1, wherein said control means comprise a rotary webcam (WEBCAM) and means for collecting historic data (LOG).

3. The device according to claim 2, wherein said electronic unit (MB) and said interface are connected via a secure communication module (COM).

4. An apparatus for local environmental measurement and control, comprising:
   a plurality of local devices (D1-Dn) according to claim 1;
   at least one remote source (INFO) of data that can be associated to local environmental quality factors (FQP1-FQPn);
   at least one remote central control unit (SER) for processing data associated to said local environmental quality factors and/or measurement data of local environmental parameters detected by said devices (D1-Dn); and
   at least one communication interface operatively connected to the remote unit (SER), to the remote source (INFO), and to the electronic unit of the local device (D1-Dn) for sending and receiving data associated to said local environmental quality factors and/or to measurement data of local environmental parameters.

5. The apparatus according to claim 4, wherein said devices (D1-Dn), said remote source (INFO), and said remote unit (SER) are connected via a telecommunication network.

6. The apparatus according to claim 5, wherein said devices (D1-Dn), said remote source (INFO), and said remote unit (SER) are connected via a protected telecommunication network.

7. A method for local environmental measurement and monitoring, comprising the steps of:
measuring the current value in time of a plurality of local environmental parameters relevant for the value of an environmental quality factor (FQP1-FQPn) of the domestic environment being monitored;
receiving from a remote source (INFO) data that can be associated to the local environmental quality factor (FQP1-FQPn);
controlling the current conditions of the domestic environment monitored that interfere with the local environmental parameters measured;
receiving repeatedly in time current measurement data of the local parameters, remote data associated to the factor (FQP1-FQPn), and current data regarding the local environmental conditions; and
calculating dynamically, by means of an adaptive algorithm, current values of the quality factor (FQP1-FQPn) of at least one environment being monitored on the basis of the local-measurement data, of remote data associated to the parameter, and of the local environmental conditions,
wherein said dynamic calculation comprises the calculation of remote data comprising data deriving from the historic memory of previous measurements made by sensors already installed,
wherein said sensors (SD11-SDnm) are integrated in a single electronic card (SCS) operatively connected to said processing unit, and comprise sensors for detecting electromagnetic fields of from 100 kHz to 3 GHz, low-frequency electromagnetic fields, radon, water composition, fine dust, $CO_2$, and noise.

8. The method according to claim 7, further comprising:
a step of remote processing of said current measurement data of the local parameters coming from at least one device (D1-Dn), of remote data associated to a factor (FQP1-FQPn) by at least one device (D1-Dn), and of current data regarding the local environmental conditions of at least one domestic environment monitored by a corresponding device (D1-Dn);
a step of calculation of corrective coefficients based upon said remote processing step; and
a step of updating of said step of calculation of the quality factors (FQP1-FQPn) on the basis of said corrective coefficients.

9. The method according to claim 8, wherein said remote data comprise data coming from social networks.

10. The method according to claim 7, wherein said remote data comprise data coming from social networks.

11. The method according to claim 10, wherein said dynamic calculation comprises the calculation of remote data comprising data deriving from the historic memory of previous measurements made by sensors already installed.

12. The method according to claim 8, wherein said dynamic calculation comprises the calculation of remote data comprising data deriving from the historic memory of previous measurements made by sensors already installed.

* * * * *